United States Patent
Singh et al.

(10) Patent No.: US 11,849,962 B2
(45) Date of Patent: Dec. 26, 2023

(54) CUTTING GUIDE WITH PROTECTIVE INSERT

(71) Applicant: Stryker European Operations Holdings LLC, Kalamazoo, MI (US)

(72) Inventors: Manoj Kumar Singh, Mahwah, NJ (US); Felix Finkenzeller, Freiburg (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 370 days.

(21) Appl. No.: 17/127,056

(22) Filed: Dec. 18, 2020

(65) Prior Publication Data

US 2021/0186533 A1 Jun. 24, 2021

Related U.S. Application Data

(60) Provisional application No. 62/953,264, filed on Dec. 24, 2019.

(51) Int. Cl.
| | | |
|---|---|---|
| *A61B 17/17* | (2006.01) | |
| *A61B 17/16* | (2006.01) | |
| *A61B 17/15* | (2006.01) | |
| *A61B 17/34* | (2006.01) | |
| *A61B 17/32* | (2006.01) | |

(52) U.S. Cl.
CPC ...... *A61B 17/1775* (2016.11); *A61B 17/1633* (2013.01); *A61B 17/151* (2013.01); *A61B 17/152* (2013.01); *A61B 17/1739* (2013.01); *A61B 17/3439* (2013.01); *A61B 2017/320052* (2013.01)

(58) Field of Classification Search
CPC ............ A61B 17/1775; A61B 17/1764; A61B 17/1635; A61B 17/151; A61B 17/1739; A61B 17/152; A61B 17/155; A61B 17/157; A61B 17/8059; A61B 17/3494; A61B 17/154; A61B 2017/320052; A61B 17/1633
USPC .......................................................... 606/84
See application file for complete search history.

(56) References Cited

U.S. PATENT DOCUMENTS

| | | |
|---|---|---|
| 6,510,334 B1 | 1/2003 | Schuster et al. |
| 7,534,263 B2 | 5/2009 | Burdulis, Jr. et al. |
| 7,618,451 B2 | 11/2009 | Berez et al. |

(Continued)

OTHER PUBLICATIONS

3D Systems, "VSPR®: Virtual Surgical Planning, integrating precision helathcare with 3D technologies for better surgical outcomes," Precision Healthcare Solutions, © 2017 by 3D Systems, Inc., 5381 South Alkire Circle, Littleton, CO 80127; 6 pages.

*Primary Examiner* — Marcela I. Shirsat
(74) *Attorney, Agent, or Firm* — Lerner David LLP

(57) ABSTRACT

A system for guiding a cutting tool in an osteotomy procedure includes a cutting block. The cutting block includes an aperture extending through a thickness of the cutting block and having a length and a width. The width of the aperture is defined between a first interior surface of the cutting block and a second interior surface of the cutting block opposing the first interior surface. The system further includes a sleeve. The sleeve includes a slot configured for receiving a sawblade and configured for insertion into the aperture of the cutting block such that the sleeve contacts either the first interior surface or the second interior surface without contacting the other interior surface.

18 Claims, 6 Drawing Sheets

(56) References Cited

U.S. PATENT DOCUMENTS

| | | |
|---|---|---|
| 8,021,368 B2 | 9/2011 | Haines |
| 8,062,302 B2 | 11/2011 | Lang et al. |
| 8,083,745 B2 | 12/2011 | Lang et al. |
| 8,105,330 B2 | 1/2012 | Fitz et al. |
| 8,641,721 B2 | 2/2014 | Aram et al. |
| 8,657,827 B2 | 2/2014 | Fitz et al. |
| 9,017,334 B2 | 4/2015 | Carroll et al. |
| 9,089,342 B2 | 7/2015 | Carroll et al. |
| 2009/0088763 A1* | 4/2009 | Aram .................. A61B 17/155 606/88 |
| 2010/0262150 A1* | 10/2010 | Lian ...................... A61B 17/15 606/103 |
| 2011/0245835 A1* | 10/2011 | Dodds ................ A61B 17/1764 606/87 |
| 2013/0296872 A1* | 11/2013 | Davison ............. A61B 17/1739 606/87 |

* cited by examiner

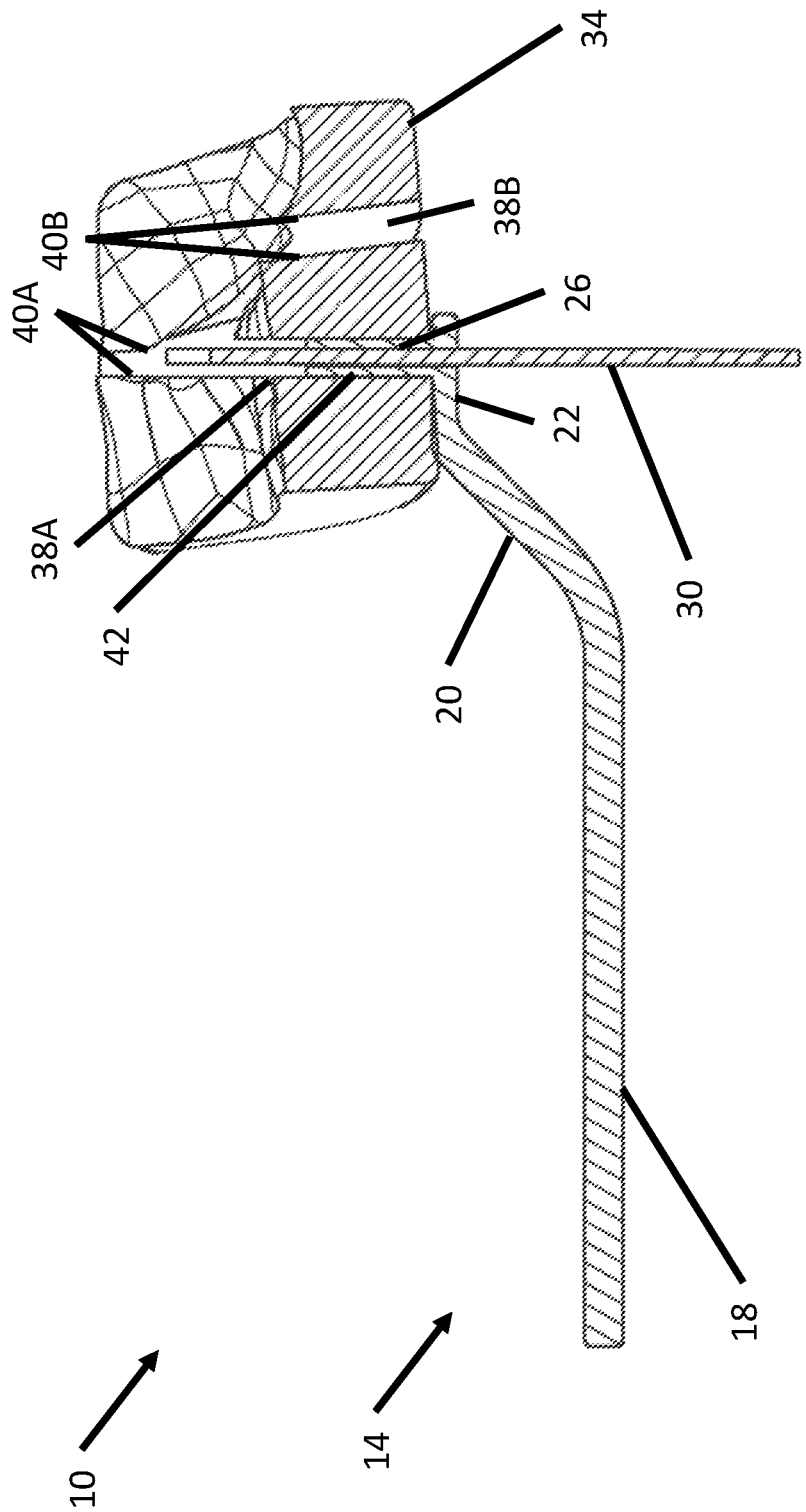

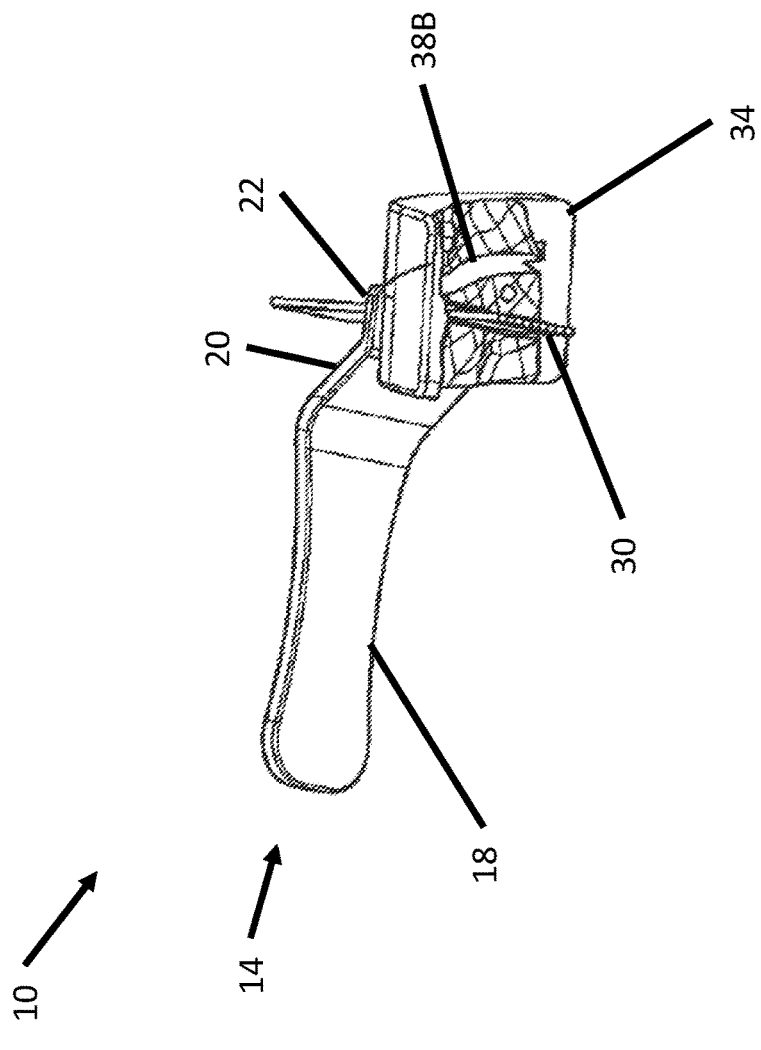
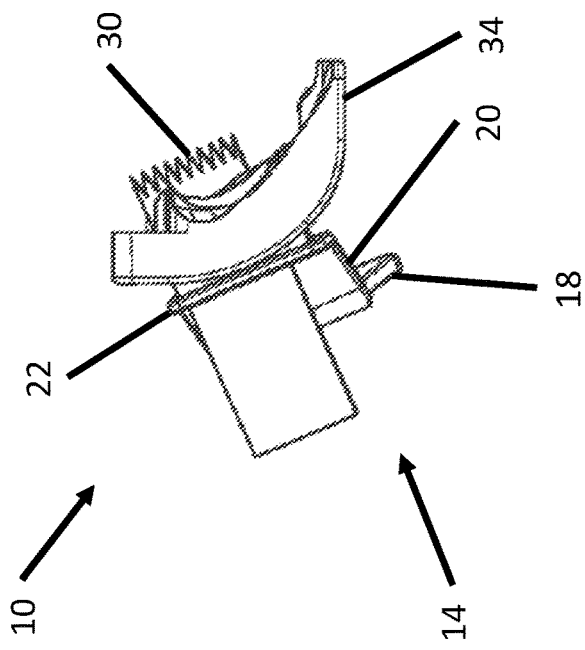
FIG. 3B
FIG. 3A

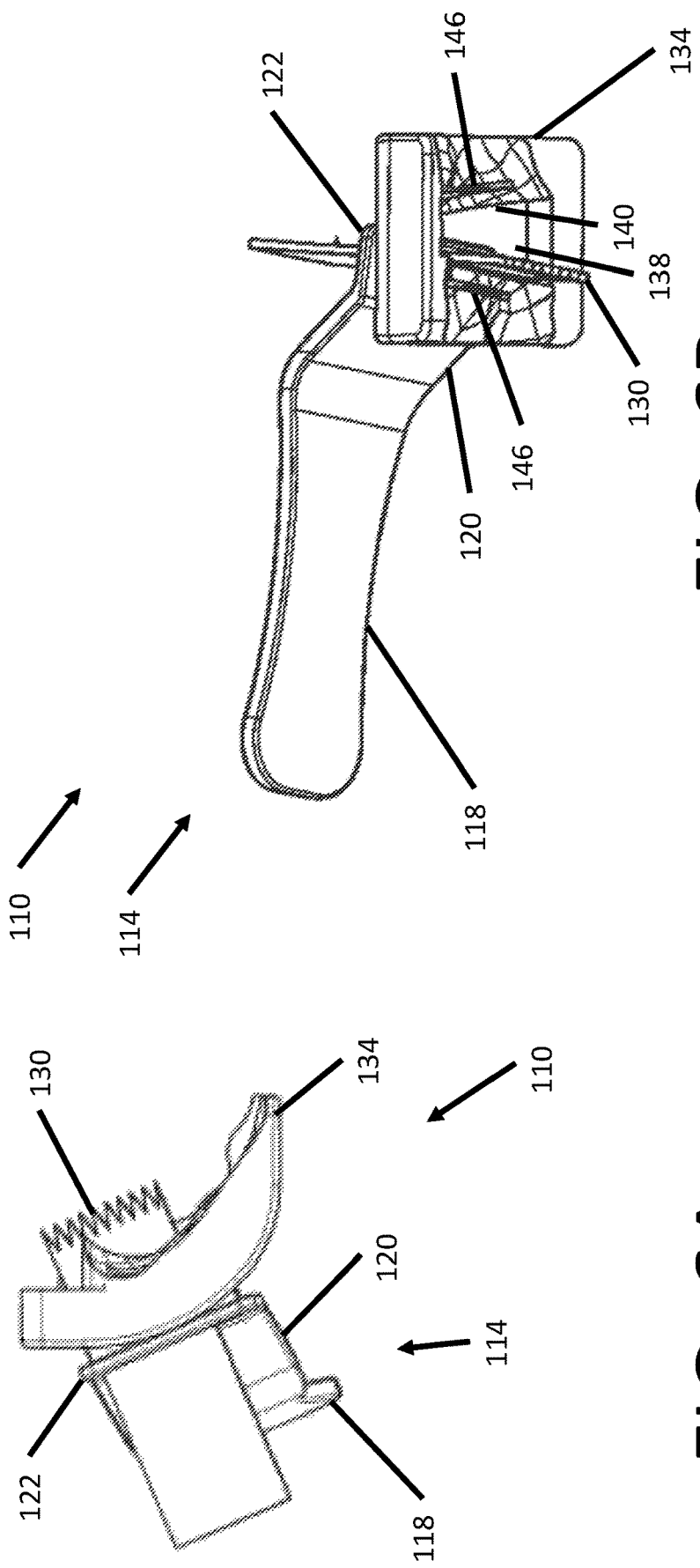

CUTTING GUIDE WITH PROTECTIVE INSERT

CROSS REFERENCE TO RELATED APPLICATIONS

The present application claims the benefit of the filing date of U.S. Provisional Patent Application No. 62/953,264 filed Dec. 24, 2019, the disclosure of which is hereby incorporated herein by reference.

BACKGROUND OF THE INVENTION

Different methods and devices have been developed in the past to enable a surgeon to remove bony material to create specifically shaped surfaces in or on a bone for various reasons such as for the attachment of various devices or objects to the bone. As the ultimate goal of any surgical procedure is to restore the body to normal function, it is critical that the quality, location, and orientation of a surgeon's cut, as well as the quality of the bone at and around the cut are sufficient for achieving proper healing of the body.

These aspects of bone resections are critical to the final location and orientation of any implant and thus play a significant role in the success or failure of any surgery or artificial joint. The quality as well as the location and orientation of the resections also directly impact the amount of bony material removed, and solutions that minimize bone loss are optimal. Additionally, with any surgical procedure, time is critical, and methods and devices that can save operating room time, are valuable. Past efforts have had variable success in properly locating and orienting resections in a quick and efficient manner as well as in maintaining the proper location and orientation of the cut during the procedure.

Oscillating sawblades used for most resections follow the path of least resistance when cutting through bone and deflect in a manner creating variations in the cut surfaces and contributing to prosthesis mal-alignment as well as poor fit between the prosthesis and the resection surfaces. Patient-specific guides have been developed to attain aspects of these goals. However, such guides have either not allowed for any flexibility for the surgeon from a preoperative plan at the time of a surgical operation or have not provided sufficient control such that resections have been made that deviated from the preoperative plan.

Accordingly, still further improvements in the alignment and operation of cutting tools for resecting bone surfaces are desired in order to increase the consistency and repeatability of bone resection procedures as is the improvement of prosthetic stability in attachment to bone.

BRIEF SUMMARY OF THE INVENTION

In accordance with an aspect of the present disclosure, a system for guiding a cutting tool in an osteotomy procedure may include a cutting block and an instrument for use with the cutting block. The cutting block may be fixable to bone, such as by pins, and the instrument may be a hand held instrument. The cutting block may include one or more apertures extending from a proximal to a distal side of the cutting block, such that bone to be cut may be accessible from the proximal side of the cutting block through the apertures. The instrument may include a sleeve receivable through the aperture, and the sleeve may be dimensioned to limit the movement, in particular the lateral movement, of a cutting tool, such as a sawblade of an oscillating bone saw as the sawblade is inserted into bone.

The one or more apertures may be closely fitted to the sleeve such that motion of the instrument relative to the cutting block when the sleeve is inserted into an aperture is limited to that permitted by withdrawal or further insertion of the sleeve into the aperture. In some arrangements, the one or more apertures may be a single aperture that is not closely fitted to the sleeve. In some arrangements, the instrument may include a tongue receivable in one or more grooves in the cutting block. The one or more grooves may be closely fitted to the tongue such that motion of the instrument relative to the cutting block when the tongue is inserted into a groove is limited to withdrawal or further insertion of the tongue into the aperture. In some arrangements, the shapes of and spacing between the aperture and the one or more grooves may cooperate with the shapes of and the spacing between the tongue and the sleeve such that motion of the instrument relative to the cutting block when the tongue is inserted into a groove is limited to withdrawal or further insertion of the tongue into the aperture.

Such limiting of motion of the instrument relative to the cutting block described above with regard to various arrangements may permit the sleeve of the instrument to reliably guide a cutting tool when the instrument is used in cooperation with the cutting block. Cuts resulting from guidance of the cutting tool by the instrument in cooperation with the cutting block may be dictated by features of the cutting block, such as the size and spacing of the one or more apertures and grooves. The cutting block may be constructed according to patient and case specific parameters such that a unique cutting block may be constructed and used for any osteotomy procedure.

In another aspect, a system for guiding a cutting tool in an osteotomy procedure may include a cutting block. The cutting block may include an aperture extending through a thickness of the cutting block and having a length and a width, the width of the aperture being defined between a first interior surface of the cutting block and a second interior surface of the cutting block opposing the first interior surface. The system may further include a sleeve. The sleeve may include a slot configured to receive a sawblade and configured for insertion into the aperture of the cutting block such that the sleeve contacts either the first interior surface or the second interior surface without contacting the other interior surface, the slot having a length and a width.

In some arrangements, a periphery of the aperture may be defined at least partially by the first and the second interior surfaces of the cutting block. Either one or both of the first and the second interior surfaces may include a flat portion and ribs protruding from the flat portion into the aperture.

In some arrangements, a profile of the aperture may be such that the width of the aperture varies along the length of the aperture, and the width of the aperture at a widest point of the aperture may be less than the length of the aperture.

In some arrangements, the aperture may have a substantially trapezoidal profile.

In some arrangements, a ratio of the width of the slot to a width of the sleeve may be less than 2:3.

In some arrangements, a ratio of a maximum length of the slot to a maximum width of the slot may be between 5:1 and 50:1.

In some arrangements, a ratio of the length of the sleeve to the length of the aperture may be less than 2:3.

In some arrangements, a height of the sleeve may extend along at least 50 percent of a thickness of the cutting block.

In some arrangements, the width of the slot may be less than 3 mm.

In some arrangements, the instrument may further include a tongue extending from the instrument. In such arrangements, the cutting block may include a groove extending into the cutting block. The groove may be shaped to receive the tongue from a proximal side of the cutting block and may be spaced from the aperture such that the tongue may be received in the groove simultaneously with the sleeve being received in the aperture.

In some arrangements, a cross-sectional shape of the groove may match a cross-sectional shape of the tongue such that motion of the instrument relative to the cutting block, while the sleeve is inserted into the aperture and the tongue is inserted into the groove such that the instrument abuts the proximal side of the cutting block, may be limited to a direction corresponding to withdrawal of the tongue from the groove.

In some arrangements, the system may further include an oscillating sawblade configured for receipt within the slot such that the sleeve substantially limits lateral movement of the oscillating sawblade to a region defined by the slot.

In accordance with another aspect, an osteotomy may be performed according to a process. In such process a cutting block may be secured to bone. The cutting block may include a proximal surface, a distal surface opposite the proximal surface and facing the bone, and an aperture extending from the proximal surface to the distal surface. In such process, an instrument may be positioned adjacent to a first interior surface of the aperture and spaced from a second interior surface of the aperture such that a first portion of a slot extending through the instrument extends within the aperture. The bone may be cut with a cutting tool while the instrument is positioned against the first interior surface of the aperture and the cutting tool is extending through the first portion of the slot such that the slot may limit lateral movement of the cutting tool to a region defined by the slot.

In some arrangements, the instrument may be stabilized during the cutting by applying force to a handle of the instrument that extends away from the cutting block.

In some arrangements, the instrument may be repositioned to the second interior surface of the cutting block after cutting the bone while the instrument is positioned against the first interior surface. The bone then may be cut along the second interior surface of the cutting block while the instrument is positioned against the second interior surface of the aperture. In some such arrangements, a first tongue of the instrument may be inserted into a first groove of the cutting block to position the instrument against the first interior surface, and the first tongue or a second tongue of the instrument may be inserted into a second groove of the cutting block to position the instrument against the second interior surface.

In some arrangements, a tongue of the instrument may be inserted into a groove of the cutting block to position the instrument against the first interior surface.

In accordance with another aspect, an osteotomy may be performed according to a process. In such process, a cutting block may be secured to bone. The cutting block may include a proximal surface, a distal surface opposite the proximal surface and facing the bone, and a plurality of apertures extending from the proximal surface to the distal surface. The a slot of an instrument may be positioned within a first aperture of the plurality of apertures. A first portion of the bone may be cut with a cutting tool while the slot of the instrument is positioned within the first aperture and the cutting tool is extending through the slot such that the slot limits lateral movement of the cutting tool to a region defined by the slot. The slot of the instrument may be repositioned within a second aperture of the plurality of apertures after the step of cutting the first portion of the bone. A second portion of the bone may be cut with a cutting tool while the slot of the instrument is positioned within the second aperture and the cutting tool extends through the slot such that the slot limits lateral movement of the cutting tool to the region defined by the slot.

In some arrangements, the plurality of apertures may be nonparallel such that surfaces of the bone formed by the cutting steps are nonparallel.

In some arrangements, the bone may form part of a foot.

In another aspect, a system for guiding a cutting tool, e.g., a surgical oscillating saw, for cutting bone, such as for an osteotomy procedure, may include a cutting block and a tool guiding instrument. The cutting block may have one or more apertures that extend through a thickness of the cutting block. The instrument may include a sleeve that may be sized to accommodate the cutting tool and to extend through at least a portion of the one or more apertures of the cutting block. The cutting block may be constructed based on patient-specific data. In this manner, either one or both of the size and orientation of any one of the one or more apertures may be configured according to the patient-specific data. Further, the cutting block may have one or more surfaces or contours that may be configured according to the patient-specific data. In one such example, the cutting block may have a bone facing surface with a contour constructed according to the patient-specific data so as to match a contour of a corresponding region of bone.

Any one of the one or more apertures may be dimensioned to restrain movement of the sleeve when the sleeve is disposed through the aperture so as to limit the possible size, angle, and rotation of a cut that may be made with the cutting tool through the sleeve while the sleeve is disposed through a given aperture. In arrangements in which the cutting block includes multiple apertures, each aperture may correspond to a cut to be made in a surgical procedure.

The cutting block may include an aperture large enough to accommodate the sleeve in multiple locations of the aperture. Such a large aperture may have multiple surfaces corresponding to cuts to be made in a surgical procedure. The cutting block and instrument may include further features, other than the aperture and sleeve, that may cooperate to guide the instrument relative to the cutting block such that the sleeve may be disposed through the aperture at only certain discrete locations. The discrete locations may correspond to preoperatively determined cuts to be made in the surgical procedure. In some arrangements, a tongue may extend from the instrument and one or more grooves having a similar shape and size as the tongue to substantially prevent lateral movement of the tongue may extend into the cutting block while, in a reversed configuration in some other arrangements, the instrument may include a groove and one or more tongues.

BRIEF DESCRIPTION OF THE DRAWINGS

A more complete appreciation of the subject matter of the present invention and various advantages thereof may be realized by reference to the following detailed description and the accompanying drawings, in which:

FIG. 2 is a cross-sectional view along lines 2-2 of FIG. 1;

FIGS. 3A and 3B are perspective views of the cutting guide system of FIG. 1;

FIGS. 6A and 6B are perspective views of the cutting guide system of FIG. 4.

DETAILED DESCRIPTION

As used herein, the term "proximal," when used in connection with a surgical tool or device, or components of a device, refers to the end of the device closer to the user of the device when the device is being used as intended. On the other hand, the term "distal," when used in connection with a surgical tool or device, or components of a device, refers to the end of the device farther away from the user when the device is being used as intended. As used herein, the terms "substantially," "generally," "approximately," and "about" are intended to mean that slight deviations from absolute are included within the scope of the term so modified.

Figure 1:
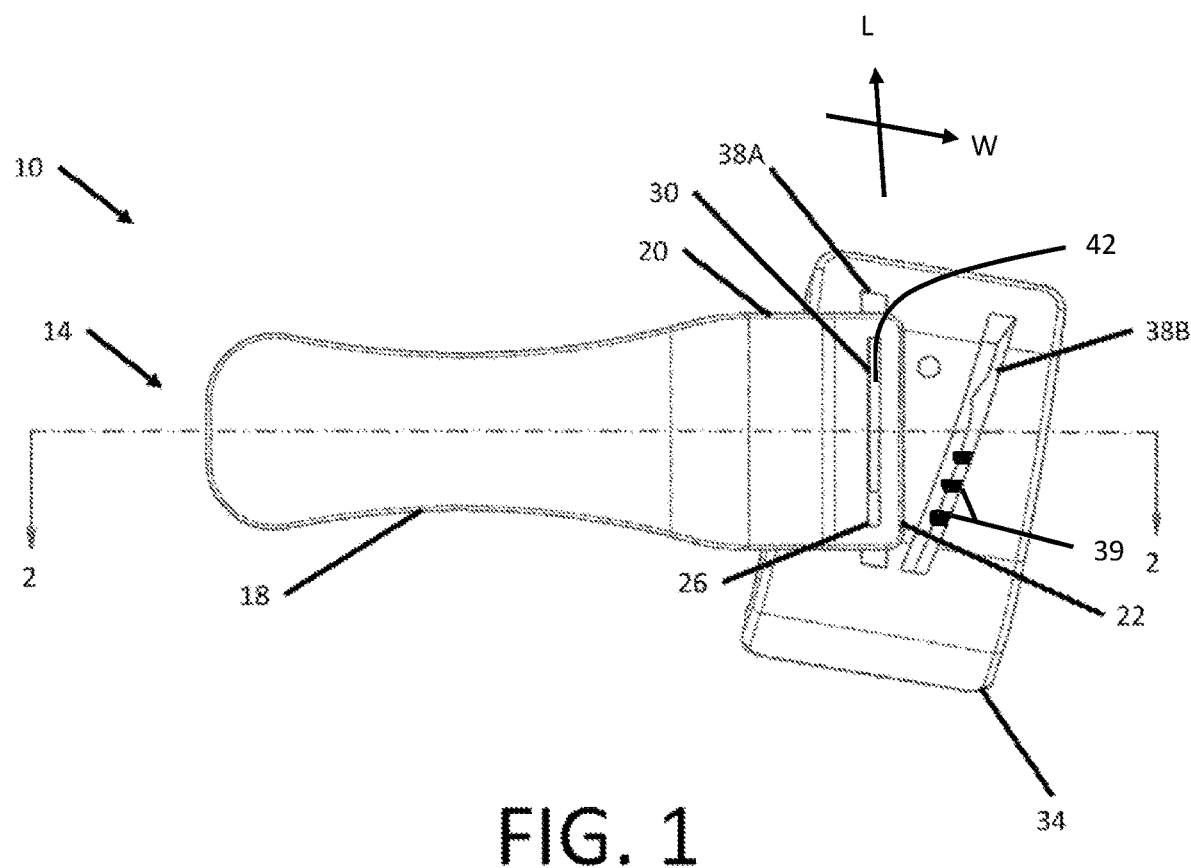
FIG. 1 is a plan view of a cutting guide system according to an embodiment.

Referring to FIG. 1, cutting guide system 10 includes instrument 14 and cutting block 34. Instrument 14 includes a handle 18, a head 22, and a neck 20 connecting handle 18 to head 22. Head 22 includes a slot 26 extending in a direction perpendicular to a length of handle 18. A sawblade 30, which in some arrangements may form part of cutting guide system 10, is shown received in slot 26 and extends in directions perpendicular to lengthwise directions of handle 18 and slot 26.

Cutting block 34 includes elongate apertures 38A, 38B. Apertures 38A, 38B are oriented relative to each other to match an intended angle for cuts in an osteotomy procedure. Either one or both of first and second interior surfaces may include ribs 39 protruding from a flat portion into apertures 38A, 38B, as shown in FIG. 1. Cutting block 34 may be constructed for a specific procedure, so the angle between apertures 38A, 38B may be both patient and case specific. Cutting block 34 may be constructed with 3D printing or additive manufacturing techniques to rapidly produce cutting block 34 to specifications unique to the patient's anatomy and condition.

As shown in FIG. 2, apertures 38A and 38B extend through cutting block 34 and are defined by opposing interior surfaces 40 of cutting block 34. Handle 18, neck 20, and head 22 of instrument 14 are each roughly planar in shape except for contours where handle 18 and head 22 meet neck 20. A sleeve 42 extends from head 22 in a direction perpendicular to the planar shape of head 22 and away from handle 18 to define a height of sleeve 42. Sleeve 42 has a length perpendicular to the height of sleeve 42 and perpendicular to the direction that handle 18 extends from head 22. The length of sleeve 42 and apertures 38A, 38B may be, for example, from 10 mm to 150 mm. Apertures 38A, 38B may have different lengths from one another, but both apertures 38A, 38B may be at least as long as sleeve 42. In some arrangements, a ratio of the length of sleeve 42 to the length of either aperture 38A, 38B may be less than 2:3. Slot 26 extends through head 22 and sleeve 42, and the sleeve is insertable through apertures 38A, 38B. As in the example shown, sleeve 42 may have a length that is shorter than lengths of apertures 38A, 38B. Apertures 38A, 38B may have differing lengths. However, both apertures 38A and 38B may be longer than sleeve 42 as shown. In one example, a ratio of the length of sleeve 42 to the length of either or both of apertures 38A, 38B, is less than 2:3. In another example, the ratio of the length of sleeve 42 to the length of either or both of apertures 38A, 38B is less than or equal to 1:1. With sleeve 42 disposed through either aperture 38A, 38B as illustrated, where the width and length of slot 26 and aperture 38A are shown in FIG. 1, slot 26 also extends through the respective aperture 38A, 38B. A length of slot 26 is aligned with the length of sleeve 42 and is less than the length of sleeve 42. The length of slot 26 may be, for example, from 10 mm to 100 mm. A width of slot 26 is perpendicular to the length of slot 26 and aligned with the width of sleeve 42 and may be, for example, 2 mm, or otherwise less than 3 mm. A ratio of the length of slot 26 to the width of slot 26 may therefore be from 5:1 to 50:1. Further, a ratio of the width of slot 26 to the width of sleeve 42 may be less than 2:3.

Slot 26 acts to guide sawblade 30 relative to aperture 38A, 38B and prevents sawblade 30 from contacting interior surfaces 40. As in the example shown, apertures 38A, 38B may have a close fit to sleeve 42 that restricts possible angular orientations of the sleeve and slot 26 relative to aperture 38A, 38B while the sleeve is disposed through the aperture. Due to the close fit of apertures 38A, 38B to sleeve 42, the orientation of apertures 38A, 38B control the orientation of cuts made using cutting guide system 10 for a given sleeve in which the relative alignment of sawblade 30 and the sleeve is fixed. Thus, the necessary cutting angles and spacing required between cuts may be specified in the unique specifications according to which cutting block 34 may be manufactured, and the resulting cutting block 34 may guide instrument 14 and sawblade 30 according to the specified angles and spacing. The necessary cutting angles, or the angle of first aperture 38A relative to the second aperture 38B may be, for example, anywhere from 0° to 70°.

As shown in FIGS. 3A and 3B, cutting block 34 of cutting guide system 10 includes a patient-specific contour. Cutting block 34 has a proximal side, referring collectively to all surfaces of cutting block 34 that face more proximally than distally, that faces instrument 14 just prior to inserting the instrument into the cutting block. The proximal side of cutting block 34 includes a smooth proximal surface with planar portions on either side of a convex curve. Apertures 38A, 38B extend along the curve such that proximal openings of apertures have a non-planar profile. Cutting block 34 also has a distal side, referring collectively to all surfaces of cutting block 34 that face more distally than proximally, from which sawblade 30 extends. The distal side of cutting block 34 includes a concave distal surface that is relatively irregular compared to the proximal surface. The irregularity may be shaped to match features of the patient near bone to be cut. Such features may be specified within the unique specifications according to which cutting block 34 may be manufactured. Further, such features are designed such that a minimum thickness of cutting block 34, defined as the smallest distance between any point on the distal side of cutting block 34 and a corresponding point on the proximal side of cutting block 34, exceeds the height of sleeve 42. The minimum thickness of cutting block 34 may exceed the height of sleeve 42 by, for example, 2 mm. Further still, such features may be designed such that a maximum thickness of cutting block 34, defined as the greatest distance between any point on the distal side of cutting block 34 and a corresponding point on the proximal side of cutting block 34, is at most twice the height of sleeve 42. The height of sleeve 42 may therefore extend along at least 50% of the thickness of cutting block 34.

In use, cutting block 34 of cutting guide system 10 may be fixed to a patient proximate to a bone, e.g., a talus, navicular, cuneiform, or metatarsal bone, or bones to be cut, and then sleeve 42 may be inserted into one of apertures 38A, 38B from a proximal side of cutting block 34. Cutting block 34 may be fixed to the patient by any suitable method for keeping cutting block 34 stable while cutting bone, such as by driving fixation pins through cutting block 34 into bone. Sawblade 30 may be disposed through slot 26 from a proximal side of head 22 before, during, or after inserting sleeve 42 into aperture 38A or 38B. After sleeve 42 is inserted into aperture 38A, 38B and sawblade 30 is disposed through slot 26, sawblade 30 may be used to cut bone. In examples where sawblade 30 is part of an oscillating bone saw, cutting bone involves activating the bone saw to cut bone within boundaries set by the interaction of sleeve 42 and aperture 38A, 38B or an interior surface 40. Cutting bone may further involve either one or both of passing sawblade 30 along slot 26 and passing sleeve 42 along aperture 38, in either case moving sawblade 30 laterally relative to cutting block 34 to perform resection of the bone. In this way, the total travel of sawblade 30 is controlled by both aperture 38 and slot 26. After cutting within one aperture 38A, 38B is complete, sleeve 42 may be removed from the one aperture 38A, 38B and inserted into another aperture 38A, 38B from the proximal side of cutting block 34, and the above described process of cutting bone may be repeated along the other of apertures 38A, 38B.

Figure 4:
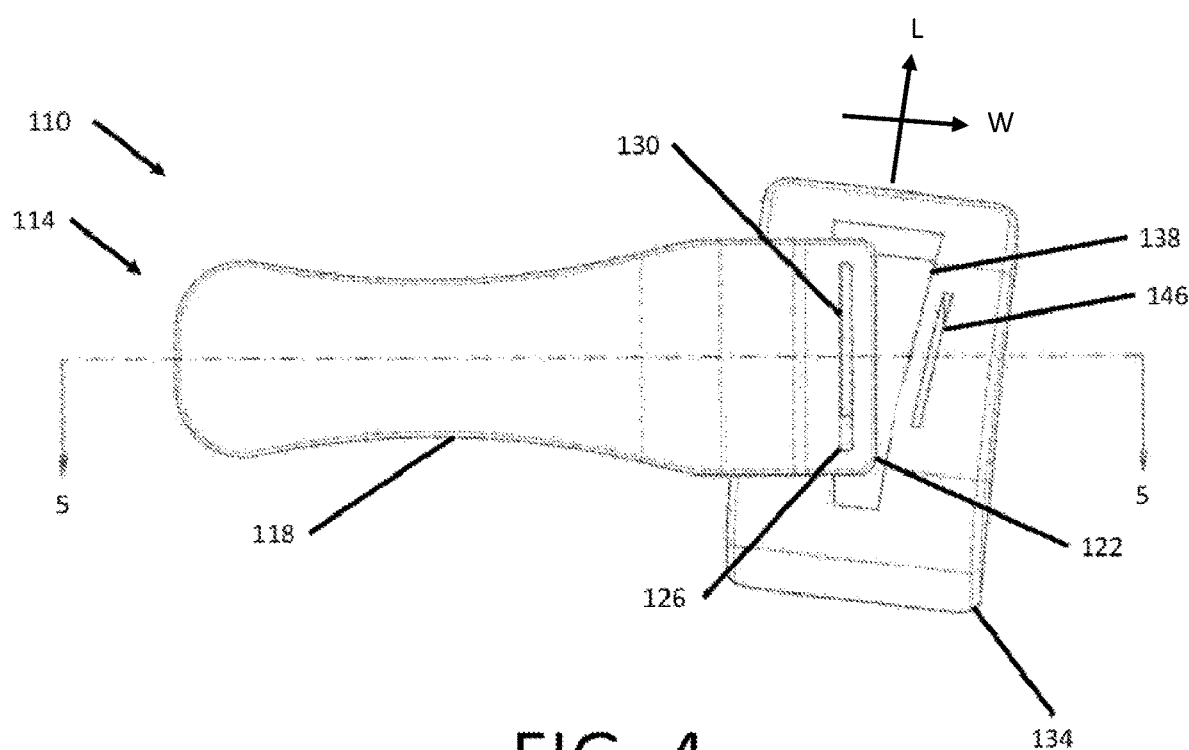
FIG. 4 is a plan view of a cutting guide system according to another embodiment.

Referring now to FIG. 4, cutting guide system 110 includes instrument 114 and cutting block 134 generally similar in form and function to instrument 14 and cutting block 34 of the arrangement of cutting guide system 10 illustrated in FIGS. 1-3B, with like elements numbered alike, (e.g., instruments 14 and 114, cutting blocks 34 and 134) except for distinctions set forth below.

Figure 5:
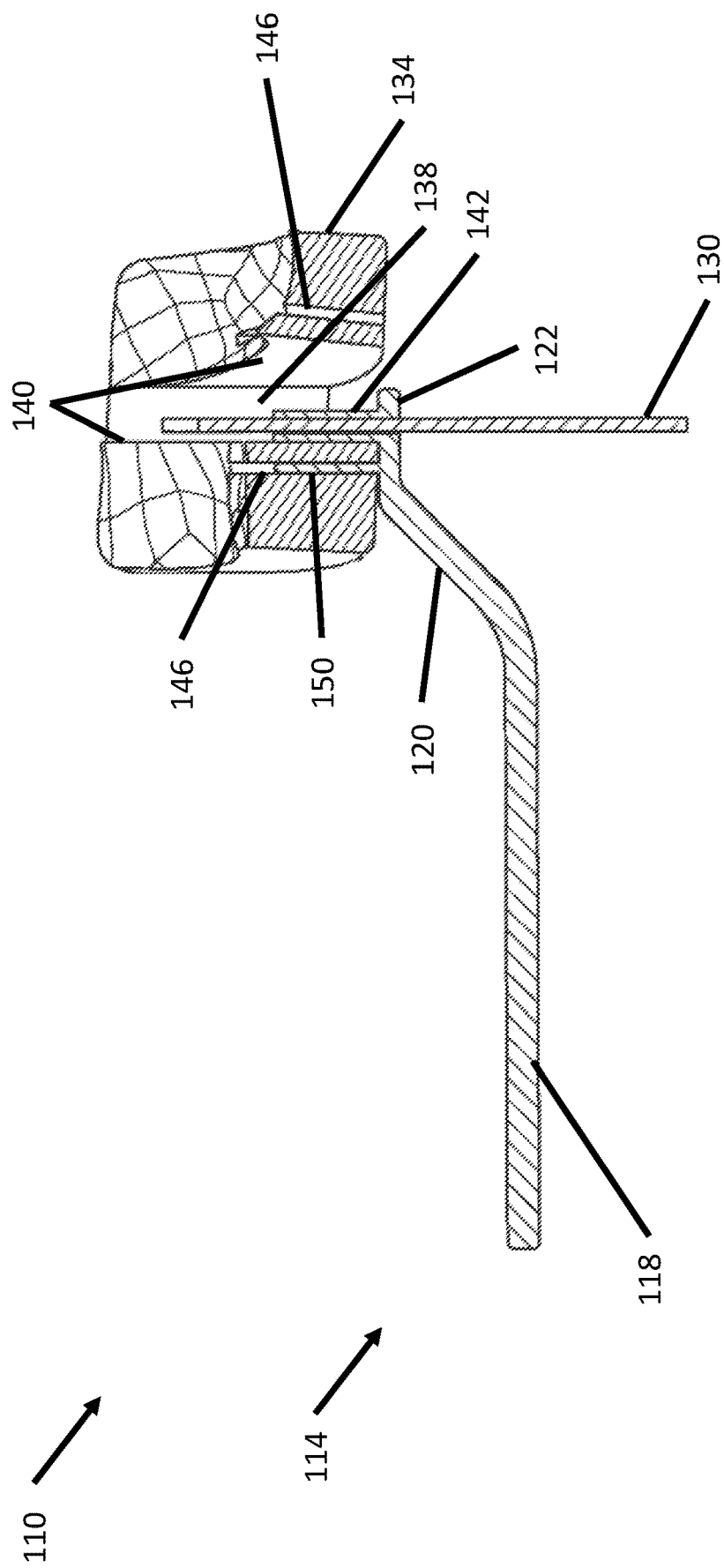
FIG. 5 is a cross-sectional view along lines 5-5 of FIG. 4.

Cutting block 134 includes a wedge shaped aperture 138 having a trapezoidal profile and two grooves 146, each groove being adjacent to and parallel to an opposing edge of aperture 138 and extending distally from a proximal surface of cutting block 134. As shown in FIG. 5, grooves 146 extend from the proximal surface of cutting block 134 to a distal surface of the cutting block. A tongue 150 extends distally from head 122 perpendicular to sleeve 126 and is insertable into groove 146. Grooves 146 are sized to have a close fit to tongue 150 such that instrument 110 is prevented from rotating or translating relative to cutting block 134 except for moving proximally or distally within the plane of sawblade 130 when tongue 150 is disposed in groove 146. Grooves 146 are spaced from aperture 138 such that sleeve 126 will be held against the adjacent one of interior surfaces 140 defining aperture 138. Grooves 146 and aperture 138 thereby cooperate to dictate possible cutting paths achievable by use of instrument 110 with cutting block 134. Locations, sizes, and orientations of grooves 146 and aperture 138 may be specified within parameters unique to a patient's anatomy and condition according to which cutting block 134 may be constructed. For example, opposing interior surfaces 140 of aperture 138 may be angled with respect to one another by, for example, anywhere from 0° to 70°, and the angle of opposing interior surfaces 140 of cutting block 134 with respect to one another may correspond to an angle of cut paths dictated by cutting block 134 with respect to one another. According to other arrangements, one or both of grooves 146 may have a greater width than a width of tongue 150 such that instrument 110 may slide along the one or both of the grooves laterally relative to cutting block 134. Because of the trapezoidal profile of aperture 138, and the alignment of grooves 146 with the non-parallel internal faces 140, such lateral sliding permits adjustment of spacing of cuts dictated by cutting block 134 without permitting any variance in the relative angle defined by the cuts, as sliding sleeve 142 along one of the non-parallel internal surfaces 140 will change the distance of sleeve 142 from the opposing internal surface 140 while maintaining a constant angle between sleeve 142 and the opposing internal surface 140.

As shown in FIGS. 6A and 6B, instrument 114 may be applied to the proximal surface of cutting block 134 such that tongue 150 extends distally into groove 146, sleeve 142 extends distally into aperture 138, and saw blade 130 extends distally through and out of aperture 138. Grooves 146 extend along an arcuate portion of cutting block 134 such that their respective openings on the proximal and distal surfaces of cutting block 134 have non-planar profiles.

Cutting guide system 110 may be used by securing or fixing patient-specific cutting block 134 to the patient proximal to a bone or bones to be cut by any known method, such as by pins or screws. Instrument 114 may be applied to cutting block 134 such that tongue 150 is disposed within one of grooves 146 and sleeve 142 is disposed within aperture 138 along one of interior surfaces 140. With instrument 114 so positioned, sawblade 130 may be used through slot 126 to cut bone along the one interior surface 140. After bone is cut along the one interior surface 140, instrument 114 may be removed such that tongue 150 is withdrawn from groove 146 and sleeve 142 is withdrawn from aperture 138. Instrument 114 may then be repositioned for a second cut, which may include reapplying instrument 114 to cutting block 134 such that tongue 150 is disposed in another of grooves 146 and sleeve 142 is disposed within aperture 138 along another of interior surfaces 140. Sawblade 130 may then be used through slot 126 to cut bone along the other interior surface 140.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for guiding a cutting tool in an osteotomy procedure, comprising:
   a cutting block, the cutting block including an aperture, a first groove, and a second groove, the aperture extending through a thickness of the cutting block and having a length and a height, the height of the aperture being defined between a first interior surface of the cutting block and a second interior surface of the cutting block opposing the first interior surface, the first and second grooves being disposed on respective opposite sides of the aperture; and
   a sleeve having a handle extending therefrom, the handle having a tongue extending therefrom, the sleeve including a slot configured to receive a sawblade and configured for removable insertion into the aperture of the cutting block such that the sleeve contacts either the first interior surface or the second interior surface without contacting the other interior surface, the slot having a width and a height,
   wherein the first and second grooves are shaped to receive the tongue, and
   wherein the tongue extends into the first groove when the sleeve is in contact with the first interior surface and into the second groove when the sleeve is in contact with the second interior surface.

2. The system of claim 1, wherein a periphery of the aperture is defined at least partially by the first and the second interior surfaces of the cutting block, and wherein either one or both of the first and the second interior surfaces include a flat portion and ribs protruding from the flat portion into the aperture.

3. The system of claim 1, wherein a profile of the aperture is such that a width of the aperture varies along the length of the aperture, and the width of the aperture at a widest point of the aperture is less than the length of the aperture.

4. The system of claim 3, wherein the profile of the aperture is substantially trapezoidal.

5. The system of claim 1, wherein a ratio of a length of the sleeve measured along a longitudinal axis of the sleeve to the length of the aperture measured along a longitudinal axis of the aperture is less than 2:3.

6. The system of claim 5, wherein a ratio of a maximum length of the slot to a maximum width of the slot is between 5:1 and 50:1.

7. The system of claim 1, wherein a height of the sleeve extends along at least 50 percent of the thickness of the cutting block.

8. The system of claim 1, wherein the aperture is a first aperture, and the cutting block further includes a second aperture extending through the thickness of the cutting block.

9. The system of claim 1, further comprising:
wherein the first and second grooves extending through the cutting block and are spaced from the aperture such that the tongue is configured to be received in either the first groove or the second groove simultaneously with the sleeve being received in the aperture.

10. The system of claim 9, wherein a cross-sectional shape of each of the first and second grooves matches a cross-sectional shape of the tongue such that motion of the instrument relative to the cutting block, while the sleeve is inserted into the aperture and the tongue is inserted into either the first -groove or the second groove such that the instrument abuts a proximal side of the cutting block, is limited to a direction corresponding to withdrawal of the tongue from either the first groove or the second groove.

11. The system of claim 1, further including an oscillating sawblade configured for receipt within the slot such that the sleeve substantially limits lateral movement of the oscillating sawblade to a region defined by the slot.

12. A method of performing an osteotomy, comprising the steps of:
securing a cutting block to bone, the cutting block including a proximal surface, a distal surface opposite the proximal surface and facing the bone, an aperture extending from the proximal surface to the distal surface, a first groove adjacent to a first interior surface of the aperture, and a second groove adjacent to a second interior surface of the aperture that is opposite to the first interior surface;
positioning an instrument adjacent to the first interior surface of the aperture and spaced from the second interior surface of the aperture such that a first portion of a slot extending through a sleeve of the instrument extends within the aperture and a tongue extending from a handle of the instrument extends within the first groove; and
cutting the bone with a cutting tool while the instrument is positioned against the first interior surface of the aperture and the cutting tool is extending through the first portion of the slot such that the slot limits lateral movement of the cutting tool to a region defined by the slot.

13. The method of claim 12, further comprising the step of stabilizing the instrument during the cutting by applying force to the handle of the instrument that extends away from the cutting block.

14. The method of claim 12, wherein the cutting step includes the steps of:
repositioning the instrument to the second interior surface of the cutting block; and
cutting the bone along the second interior surface of the cutting block while the instrument is positioned against the second interior surface of the aperture and the tongue is positioned within the second groove.

15. The method of claim 12, wherein the bone forms part of a foot.

16. A method of performing an osteotomy, comprising the steps of:
securing a cutting block to bone, the cutting block including a proximal surface, a distal surface opposite the proximal surface and facing the bone, a plurality of apertures extending from the proximal surface to the distal surface, and at least a first aperture of the plurality of apertures having a first groove disposed adjacent therewith, and a second groove disposed opposite to the first groove;
positioning a slot extending through a sleeve of an instrument within the first aperture of the plurality of apertures and a tongue extending from a handle of the instrument within the first groove;
cutting a first portion of the bone with a cutting tool while the slot of the instrument is positioned within the first aperture and the cutting tool is extending through the slot such that the slot limits lateral movement of the cutting tool to a region defined by the slot;
repositioning the slot of the instrument within a second aperture of the plurality of apertures after the step of cutting the first portion of the bone; and
cutting a second portion of the bone with a cutting tool while the slot of the instrument is positioned within the second aperture and the cutting tool is extending through the slot such that the slot limits lateral movement of the cutting tool to the region defined by the slot.

17. The method of claim 16, wherein the plurality of apertures are nonparallel such that surfaces of the bone formed by the cutting steps are nonparallel.

18. The method of claim 16, wherein the bone forms part of a foot.

* * * * *